(12) United States Patent
Stössel et al.

(10) Patent No.: US 7,223,484 B2
(45) Date of Patent: May 29, 2007

(54) 2,1,3-BENZOTHIADIAZOLES FOR USE AS ELECTRONIC ACTIVE COMPONENTS

(75) Inventors: Philipp Stössel, Frankfurt (DE); Amir Parham, Frankfurt (DE); Horst Vestweber, Gilserberg-Wintersscheid (DE); Hubert Spreitzer, Viernheim (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 10/519,967

(22) PCT Filed: Jun. 14, 2003

(86) PCT No.: PCT/EP03/06287

§ 371 (c)(1),
(2), (4) Date: Apr. 14, 2005

(87) PCT Pub. No.: WO2004/002970

PCT Pub. Date: Jan. 8, 2004

(65) Prior Publication Data

US 2006/0052612 A1    Mar. 9, 2006

(30) Foreign Application Priority Data

Jun. 29, 2002  (DE)  ................................ 102 29 370

(51) Int. Cl.
H01J 1/62       (2006.01)
C07D 285/14   (2006.01)

(52) U.S. Cl. .................. 428/690; 428/917; 548/126; 548/134; 313/504; 313/506; 257/40; 257/E51

(58) Field of Classification Search ............... 313/503, 313/504, 506, 509; 257/301.35, 40, E51; 428/690, 917; 252/500; 514/241.1, 242.1, 514/249, 243.2, 265.1, 275; 548/126, 134

See application file for complete search history.

(56) References Cited

U.S. PATENT DOCUMENTS

| 4,053,617 A | * | 10/1977 | Eichenberger et al. ...... 514/362 |
| 4,539,507 A | | 9/1985 | VanSlyke et al. |
| 5,151,629 A | | 9/1992 | VanSlyke |
| 6,153,763 A | * | 11/2000 | Kurahashi et al. ....... 548/333.5 |
| 6,476,265 B1 | | 11/2002 | Spreitzer et al. |
| 6,756,367 B2 | * | 6/2004 | Neumann ................... 514/183 |
| 2003/0099785 A1 | | 5/2003 | O'Neill et al. |

FOREIGN PATENT DOCUMENTS

| JP | 05222361 | | 8/1993 |
| JP | 2000282024 | | 10/2000 |
| JP | 2001-097949 | * | 4/2001 |
| JP | 2001097949 | | 4/2001 |
| JP | 2003-104976 | * | 4/2003 |
| JP | 2003104976 | | 4/2003 |
| JP | 2003265054 | | 9/2003 |
| WO | WO-99/12888 | | 3/1999 |
| WO | WO-00/46321 | | 8/2000 |

OTHER PUBLICATIONS

Yamishita et al. Synthesis and Properties of Benzobis(thiadiazole)s with Nonclassical pi-electron ring structures; Tetrahedron, vol. 53, No. 29, Jul. 1997, pp. 10169-10178.*

(Continued)

*Primary Examiner*—Rena Dye
*Assistant Examiner*—Camie S. Thompson
(74) *Attorney, Agent, or Firm*—Connolly Bove Lodge & Hutz LLP

(57) ABSTRACT

The present invention describes novel 2,1,3-benzothiadiazole-containing compounds. Such compounds can be used as active components (=functional materials) in a variety of different applications which can in the widest sense be considered part of the electronics industry.

21 Claims, 4 Drawing Sheets

Data for the OLED of example 1

OTHER PUBLICATIONS van Mulekom et al., Development in the chemistry and band gap engineering of donor-acceptor substituted conjugated polymers, Materials Science and Engineering, 32(2001) pp. 1-40.*

Yamashita et al., "Synthesis and Properties of Benzobis(thiadiazole)s with Nonclassical π-Electron Ring Systems", *Tetrahedron*, vol. 53, No. 29, pp. 10169-10178 (1997).

van Mullekom et al., "Band-Gap Engineering of Donor-Acceptor-Substituted π-Conjugated Polymers", Chem. Eur. J., vol. 7, No. 4, pp. 1235-1243 (1998).

Jayakannan et al., "Synthesis and Structure-Property Relationship of New Donor-Acceptor-Type Conjugated Monomers and Polymers on the Basis of Thiophene and Benzothiadiazole", *Journal of Polymer Science*: Part A: Polymer Chemistry, vol. 40, pp. 251-261 (2002).

Blanchard et al., "New synthetic strategies towards conjugated NLO-phores and fluorophores", *Synthesis Metals*, vol. 119, pp. 527-528 (2001).

Kitamura et al., "Design of Narrow-Bandgap Polymers, Syntheses and Properties of Monomers and Polymers Containing Aromatic-Donnor and o-Quinoid-Acceptor Units", Chem. Mater., vol. 8, pp. 570-578 (1996).

* cited by examiner

Figure 1: Data for the OLED of example 1
Efficiency as a function of brightness
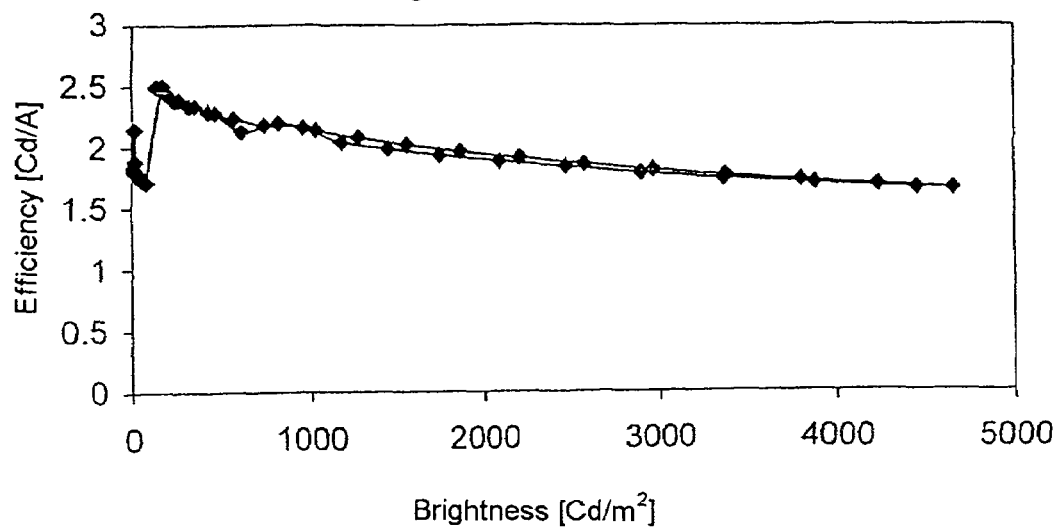
Figure 2: Data for the OLED of example 1
EL spectrum
CIE: x= 0.65 · y= 0.35
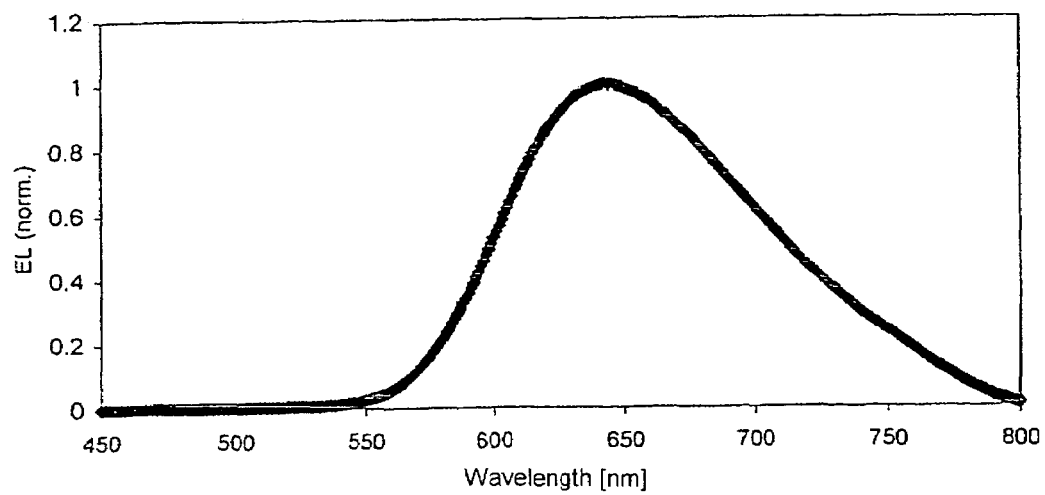

Figure 3: Data for the OLED of example 1
Brightness as a function of time
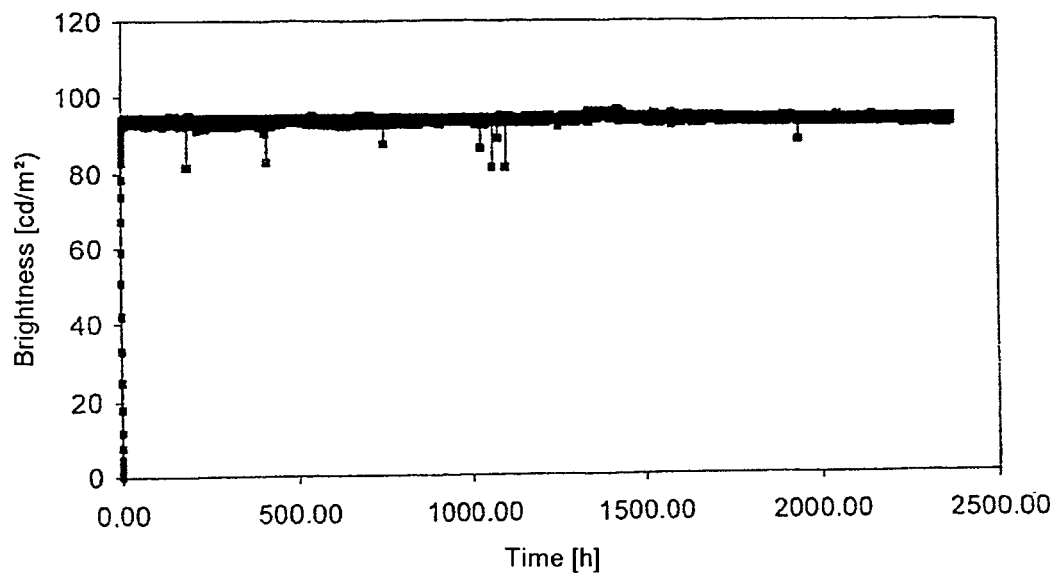
Figure 4: Data for the OLED of example 2
Efficiency as a function of brightness
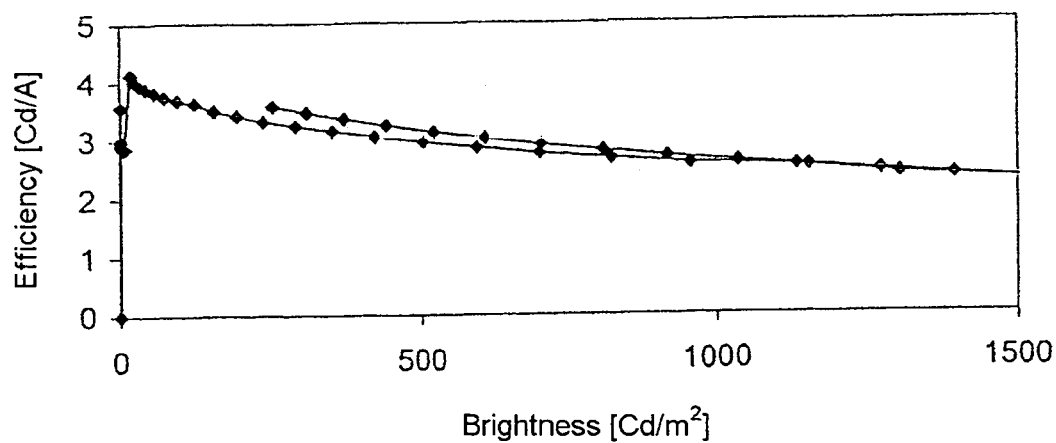

Figure 5: Data for the OLED of example 2
EL spectrum
CIE: x= 0.64 · y= 0.36
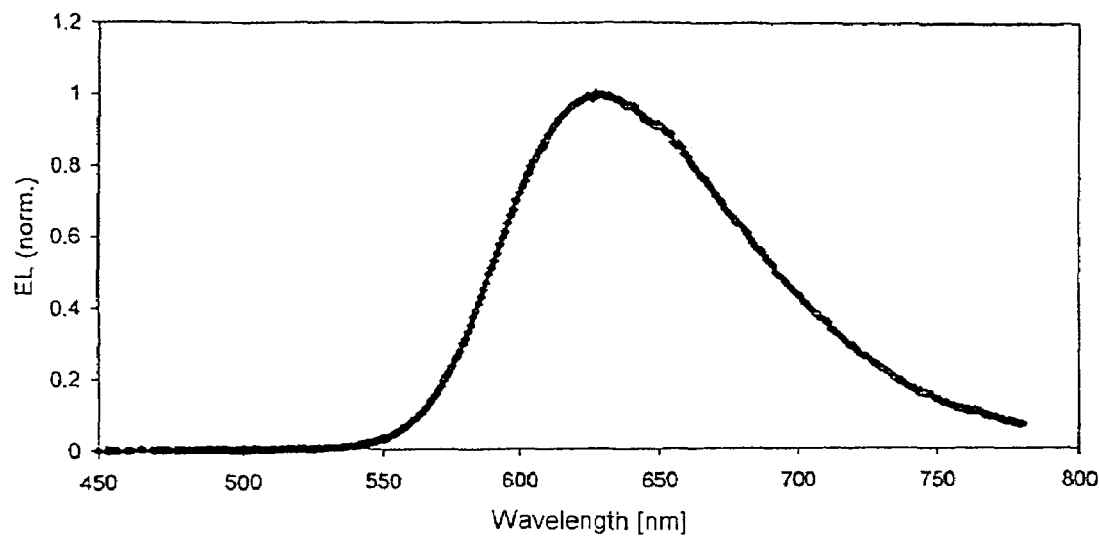
Figure 6: Data for the OLED of example 2
Brightness as a function of time
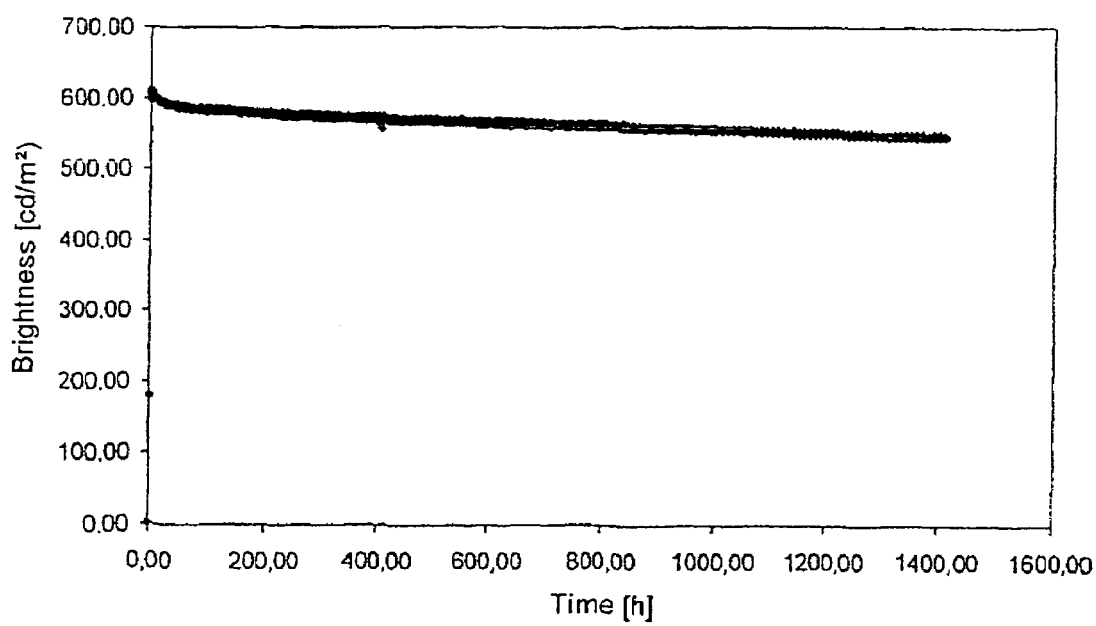

Figure 7: Data for the OLED of example 3
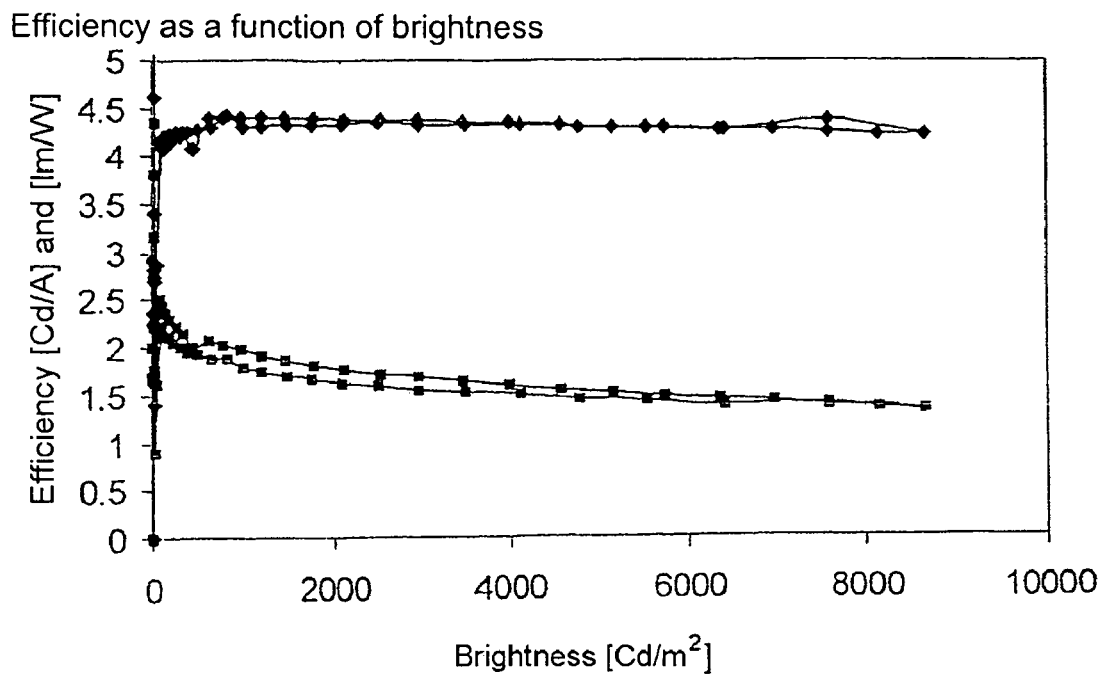
Figure 8: Data for the OLED of example 3
EL Curve
CIE: x = 0.15, y = 0.16
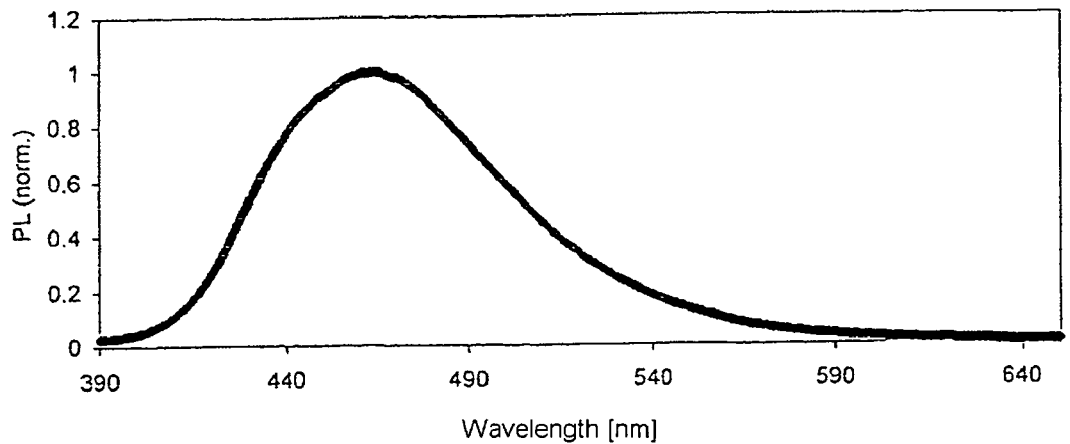

2,1,3-BENZOTHIADIAZOLES FOR USE AS ELECTRONIC ACTIVE COMPONENTS

This application is a national stage application (under 35 U.S.C. 371) of PCT/EP03/06287 filed Jun. 14, 2003 which claims benefit to German application Serial No. 102 29 370.8 filed Jun. 29, 2002.

Organic compounds will in the near future be employed as active components (=functional materials) in a variety of different applications which can in the widest sense be considered part of the electronics industry.

In the case of the organic electroluminescence devices based on organic components (for general description of the structure, cf. U.S. Pat. Nos. 4,539,507 and 5,151,629) or their individual components, viz. organic light-emission diodes (OLEDs), introduction onto the market has already occurred, as the car radios with "organic display" obtainable from Pioneer demonstrate. Further such products will be introduced shortly. However, significant improvements are still necessary here in order for these displays to effectively compete with or to surpass the liquid crystal displays (LCDs) which currently dominate the market.

Important conditions for practical use are, in particular, a long operating life, a high stability to heat and a low use and operating voltage in order to make mobile applications possible.

The general structure of organic electroluminescence devices is described, for example, in U.S. Pat. Nos. 4,539, 507 and 5,151,629.

An organic electroluminescence device usually comprises a plurality of layers which are preferably applied on top of one another by means of vacuum methods. These individual layers are:

1. a support plate=substrate (usually glass or plastic film);
2. a transparent anode (usually indium-tin oxide, ITO);
3. a hole injection layer (=HIL): e.g. one based on copper phthalocyanine (CuPc), conductive polymers such as polyaniline (PANI) or polythiophene derivatives (e.g. PEDOT);
4. a hole transport layer (=HTL): usually one based on triarylamine derivatives;
5. an emission layer (=EML): this layer can coincide partly with layers 4 or 6, but usually comprises fluorescent dyes or host molecules doped with fluorescent dyes;
6. an electron transport layer (=ETL): mostly on the basis of aluminum tris-8-hydroxyquinoxalinate ($AIQ_3$);
7. an electron injection layer (=EIL): this layer can coincide partly with the layer 6 or a small part of the cathode is specifically treated or specifically deposited;
8. a cathode: here, metals, metal combinations or metal alloys having a low work function are generally used, e.g. Ca, Ba, Mg, Al, In, Mg/Ag.

This overall device is, depending on the application, structured, provided with contacts and finally hermetically sealed since the life of such devices is generally reduced drastically in the presence of water and/or air.

On application of an appropriate electric potential, holes from the anode and electrons from the cathode are injected into the device and there meet to produce an excited state. This can break down with emission of light. This light is emitted through the transparent anode. In some applications it can also be useful to reverse the arrangement, i.e. to use a (semi)transparent cathode when the anode is, for example, applied to an opaque substrate (for example a silicon chip).

In either case, the individual OLED will emit light which has a color determined by the EML. It is in this way possible, depending on the EML, to generate the three basic colors (blue, green, red).

A suitable combination of various individual OLEDs then makes it possible to produce a variety of devices ranging from individual light-emitting diodes through simple segmented displays through more complicated matrix displays to full-color, large-format displays/VDUs.

The EML functional materials of the abovementioned OLEDs have been or are being intensively optimized. Despite intensive optimization, the characteristic data of the above-described OLEDs have a number of weak points among which two weak points, viz. the short life of the EML materials and the unfavorable efficiency-brightness curves, have proven to be a particular hindrance in the implementation of OLED technology in commercial products:

1) The realistic life of the OLED materials available at present under conditions close to practice is severely limited. The life (time after which the luminance has dropped to 50% of the initial luminance) in the red at constant current density and an initial luminance of 100 $Cd/cm^2$ is at best a few thousand hours. In the blue, on the other hand, usually only a few hundred to at best from two to three thousand hours are achieved at an initial luminance of 100 $Cd/cm^2$.

These lives are insufficient for practical applications and hinder the introduction of OLED devices on the market.

2) It can be seen from the efficiency-brightness curves of conventional materials that the efficiency decreases greatly with increasing brightness. This means that the high brightnesses necessary in practice can be achieved only by means of a high power consumption. However, high power consumptions require high battery powers in portable appliances (mobile phones, laptops, etc.). In addition, the high power consumption, which is mostly converted into heat, can lead to thermal damage to the display.

These deficiencies of the prior art lead to the following objects of the invention: provision of EML materials having a long operating life at industrially feasible luminances in combination with flat efficiency-brightness curves, i.e. materials which display good efficiencies even at high brightnesses.

It has surprisingly been found that particular compounds comprising the 2,1,3-benzothiadiazole unit have excellent properties for use as EML (as pure material or as dopant in a host molecule matrix).

Compounds comprising the 2,1,3-benzothiadiazole unit are subject matter of the present invention. These compounds have the following properties:

1. The emission color of the compounds of the invention can be adjusted over the entire visible region, i.e. from deep blue to deep red, by choice of an appropriate substitution pattern (cf. examples).
2. The 2,1,3-benzothiadiazole-containing compounds of the invention lead, when appropriate devices are used, to excellent operating lives, as example R1 and the operating life measurements carried out therewith show by way of example. Even after 2500 hours of operation, no significant drop in the luminance is observed. This unique behavior resulting from the 2,1,3-benzothiadiazole unit indicates expected lives of >>10 000 hours.
3. The 2,1,3-benzothiadiazole-containing compounds of the invention when used as EML material in electroluminescence devices lead to high efficiencies of the devices, in particular at the industrially desirable high current densities. They make very good efficiencies possible even at high current densities.

4. The 2,1,3-benzothiadiazole-containing compounds of the invention can be prepared with good reproducibility in reliably high purity and display no batch-to-batch fluctuations.

5. The 2,1,3-benzothiadiazole-containing compounds of the invention have a high thermal stability. Choice of suitable substitution patterns enables glass transition temperatures of greater than 100° C. to be achieved.

6. The 2,1,3-benzothiadiazole-containing compounds of the invention have excellent solubility in organic solvents. These materials can thus be processed from solution by means of coating or printing techniques. In a preferred embodiment, solutions can be processed together with one or more other compounds which can have either a low molecular weight or a relatively high or high molecular weight. Even in conventional processing by evaporation, this property is advantageous since it makes cleaning of the equipment or the masks used considerably easier.

In addition to the very good properties as EMLs, it has surprisingly been found that particular 2,1,3-benzothiadiazole-containing compounds display excellent properties when used as ETL, as HBL (hole blocking layer) or as host material in the EML, particularly as host material in new types of phosphorescent OLED devices. The use of these compounds in phosphorescent organic electroluminescence devices (for general structure and mode of operation, see: M. A. Baldo, S. Lamansky, P. E. Burrows, M. E. Tompson, S. R. Forrest, Applied Physics Letters, 1999, 75, 4–6) is therefore likewise subject matter of the present invention.

Looking at the prior art in respect of ETL materials, it is conspicuous that $AlQ_3$ is used virtually exclusively as ETL in all devices. This compound is also, as mentioned above, frequently used additionally as host material for the EML. Although many attempts have been made to replace this compound by other substances, this has not been successful to date. Up to the present time, $AlQ_3$ still represents the best compromise for the differing requirements. Thus, the compound has not only a high thermal stability (glass transition temperature $T_g$~190° C.), an obviously usable band position and an acceptable quantum efficiency for fluorescence in the solid state (about 40%). However, a negative aspect is the intrinsic color (absorption: yellow) on the compound which can, particularly in the case of blue OLEDs, lead to color shifts as a result of fluorescence absorption and reemission. This is a particular disadvantage in the abovementioned device structure in which the light is emitted through the cathode, i.e. through the ETL too. Here, blue OLEDs can only be produced with severe deterioration in efficiency or color position. The usability of $AlQ_3$ in the new types of phosphorescent OLEDs has also not been conclusively clarified.

A further disadvantage of the use of $AlQ_3$ is the instability toward holes which has now become known from the literature [cf., for example, Z. Popovic et al., Proceedings of SPIE, 1999, 3797, 310–315] and can always lead to problems in the device in long-term use.

A critical practical disadvantage of $AlQ_3$ is the strongly hygroscopic nature of this compound. $AlQ_3$ which is synthesized and stored under normal conditions always contains, in addition to the hydroxyquinoline ligand, one mol ecule of water per molecule of complex [cf., for example: H. Schmidbaur et al., Z. Naturforsch. 1991, 46b, 901–911]. This is extremely difficult to remove. For use in OLEDs, $AlQ_3$ therefore has to be purified in complicated, multistage sublimation processes and subsequently be stored and handled with exclusion of water in a protective gas atmosphere. Furthermore, large fluctuations in the quality of individual $AlQ_3$ batches and also poor storage stability have been found (S. Karg, E-MRS Conference May 30, 2000–Jun. 2, 2000 Strassbourg).

$AlQ_3$ is likewise used as ETL in the new types of phosphorescent OLEDs, and in addition the question of the host material for the actual triplet emitters has still not been clarified at all. The use of only a few materials (4,4'-biscarbazolylbiphenyl, polyvinylcarbazole and a triazole derivative) has been reported to date. However, the operating lives are still greatly in need of optimization.

The 2,1,3-benzothiadiazole-containing compounds of the invention which can be used as ETL, as HBL or as host material in the EML are distinguished, especially compared to $AlQ_3$ and the few host materials known to date for phosphorescent OLEDs, by the following properties:

1. They are colorless or virtually colorless; this means that their UVA/IS absorption in the wavelength range from 400 to 700 nm is negligible. In electroluminescence devices according to the invention, this leads to better color purity and high efficiency. This has the advantage that they lead, especially in blue OLEDs, to no color shift or reduction in efficiency. A further advantage is naturally their use as host or ETL material in inverted (cf. above) device geometries.

2. The 2,1,3-benzothiadiazole-containing compounds of the invention when used as host or ETL material in the electroluminescence devices according to the invention lead to high efficiencies which are, in particular, independent of the current densities used. Very good efficiencies are thus made possible even at high current densities.

3. The 2,1,3-benzothiadiazole-containing compounds of the invention have a high oxidation stability. When they are used in appropriate devices according to the invention, this can lead to a significant increase in the operating life. Furthermore, the production of these devices becomes simpler.

4. The 2,1,3-benzothiadiazole-containing compounds of the invention are not noticeably hygroscopic and display a high stability to atmospheric oxygen. Storage for a number of days or weeks in the presence of air and water vapor does not lead to any changes in the substances. Uptake of water by the compounds cannot be detected. This naturally has the advantage that the substances can be purified, transported, stored and prepared for use under simplified conditions. Use does not, in contrast to operations employing $AlQ_3$, have to take place entirely under protective gas.

In addition, as described above for use as EML materials, they can be prepared reproducibly in good yields and are thermally stable and readily soluble in organic solvents.

The use of molecularly defined, uniform, low molecular weight (molar mass<5000 g/mol) 2,1,3-benzothiadiazole-containing compounds in OLEDs is novel.

The invention provides compounds comprising at least one structural unit of the formula (I),

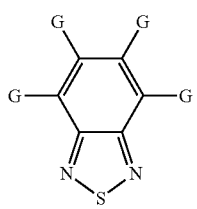

Formula (I)

characterized in that the group G is hydrogen, fluorine and/or an organic radical, the compounds belong to the idealized point group $S_n$, $C_n$, $C_{nv}$, $C_{nh}$, $D_n$, $D_{nh}$ or $D_{nd}$ with n=2, 3, 4, 5 or 6, the molar masses are in the range from 450 g/mol to 5000 g/mol and the melting points are above a temperature of 190° C., with the proviso that they do not contain a macrocycle.

The term point group as used here is a term employed in group theory, as described, for example, in: F. A. Cotton, Chemical Applications of Group Theory, 3$^{rd}$ Edition, New York, Wiley, 1990.

For the purposes of the present invention, a macrocycle is a ring having more than eight ring atoms (J.-M. Lehn, Dietrich, Viont, Makrocyclic Compounds Chemistry, Weinheim, V C H Verlag, 1992 and Tetrahedron 1995, 51, 9241–9284, 9767–9822).

The 2,1,3-benzothiadiazole-containing compounds of the invention are highly suitable for use as electroluminescence materials. They can likewise be used as dopants in many host materials.

Corresponding OLEDs in which the 2,1,3-benzothiadiazole-containing compounds of the invention are present have both a long life and a high EL efficiency.

Prerequisites for this are the above-described symmetry properties. The 2,1,3-benzothiadiazole-containing compounds have to have at least one two-fold or higher rotational axis since in these cases the quantum yield of the fluorescence and thus the quantum yield of the electroluminescence is particularly large and is generally significantly higher than in the case of unsymmetrical compounds of the points $C_1$ and $C_s$.

A further necessary prerequisite which suitable OLED materials have to fulfill, especially when they are applied by vacuum vapor deposition or vapor deposition in a carrier gas stream, is a molar mass in the range from 450 g/mol to 5000 g/mol. If the molar mass is below the abovementioned range, the vapor pressure is so great that the vacuum equipment will be seriously contaminated even at low temperatures. Secondly, experience has shown that when the upper molar mass limit is exceeded, decomposition-free vaporization is no longer possible.

Closely linked to the molar mass are the melting points of the compounds. These have to be above about 190° C., since only then is sufficiently slow and uniform vaporization ensured and only this leads to homogeneous, vitreous films. However, vitreous films are an indispensable prerequisite for functional OLEDs. The melting point of a compound is the temperature at which the phase transition from the solid state to the liquid state takes place.

In addition, a sufficiently high glass transition temperature in the range above 100° C. is a necessary prerequisite for OLEDs which are to be stable over the long term. Experience shows that in suitable organic materials the glass transition temperature is typically at least 60°–90° C. below the melting point, so that a melting point of 190° C. represents a lower limit for this property, too.

Furthermore, the 2,1,3-benzothiadiazole-containing compounds must not contain any macrocyclic structure, since otherwise they will efficiently complex the palladium used during the synthesis and thus deactivate the coupling catalyst. In addition, these complexes are difficult to separate quantitatively from the product, so that purification of the corresponding compounds is no longer feasible.

The invention likewise provides compounds of the formulae (II) and (III),

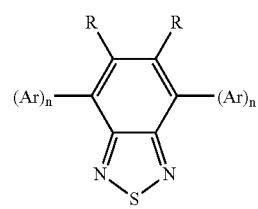

Formula (II)

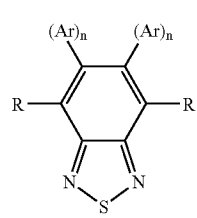

Formula (III)

where the symbols and indices have the following meanings:

the radicals R are identical on each occurrence and are each H, F, CN, a straight-chain or branched or cyclic alkyl or alkoxy group having from 1 to 20 carbon atoms, where one or more nonadjacent $CH_2$ groups may be replaced by —O—, —S—, —$NR^1$ or —$CONR^2$— and one or more H atoms may be replaced by F;

the radicals Ar are identical or different on each occurrence and are each an aryl or heteroaryl group which has from 3 to 30 carbon atoms and may be substituted by one or more nonaromatic radicals R; where a plurality of substituents R, both on the same ring and on the two different rings, may in turn together form a further monocyclic or polycyclic ring system;

$R^1$, $R^2$ are identical or different and are each H or an aliphatic or aromatic hydrocarbon radical having from 1 to 20 carbon atoms;

n is from 1 to 10, preferably from 1 to 6, particularly preferably 1, 2 or 3.

The property profile of the abovementioned compounds of the formula (II) or (III) in respect of the requirements for OLED applications can be tailored by choice of the substituents Ar. Thus, for example, appropriate choice of the substituent Ar enables the emission color to be set in a targeted manner over the entire visible region from deep red to deep blue (see examples).

The invention likewise provides compounds of the formula (IV),

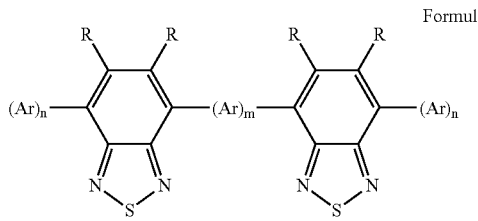

Formula (IV)

where the symbols and indices R, Ar, $R^1$, $R^2$ and n are as defined above and m has the following meaning:
m is from 0 to 4, preferably 1 or 2.

Repetitive concatenation of unconjugated emitting subunits which is achieved, inter alia, by multiple repetition of 2,1,3-benzothiadiazole units and aromatic radicals Ar, viz. compounds of the formula (IV), leads to materials having a correspondingly short emission wavelength (blue emission color) combined with a high molar mass which result in the abovementioned positive properties with regard to vaporization and the glass transition point.

A balanced charge carrier injection (hole or electron injection) into the emission layer and a balanced charge carrier transport in the emission layer are basic prerequisites for efficient OLEDs having a long life. Since the 2,1,3-benzothiadiazole-containing compounds are, as indicated above, good electron conductors, it can in specific cases be found to be advantageous to incorporate hole-conducting units, e.g. triarylamine units as in compounds of the formulae (V) and (VI) in a targeted manner into the emitter material for the EML. Accordingly, compounds of the formula (V) and (VI) are likewise subject matter of the invention:

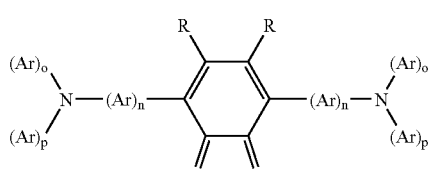

Formula (V)

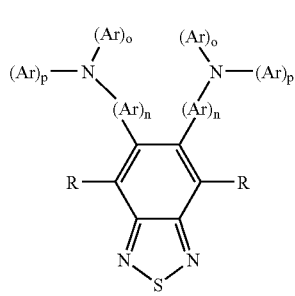

Formula (VI)

where the symbols and indices R, Ar, $R^1$, $R^2$ and n are as defined above and o and p have the following meanings:
o is from 1 to 3, preferably 1;
p is from 1 to 3, preferably 1.

Novel 2,1,3-benzothiadiazole-containing compounds of the formulae (V) and (VI) but also (VII), (VIII) and (IX), (X) and (XI) (see below) in which the 2,1,3-benzothiadiazole unit and the joined-on aromatic/heteroaromatic are strongly twisted relative to one another have a low-lying HOMO (<5.5 eV relative to the vacuum level) and thus a pronounced stability to oxidation. Accordingly, they are particularly suitable for use as ETL, HBL and also as host material in the EML. In addition, with an appropriate choice of the aromatic/heteroaromatic radicals Ar, they are able to generate triplet states by electron-hole recombination and these can then efficiently be transferred to phosphorescent emitters present as dopants. This property is particularly advantageous in the use of compounds of the formulae (VII) and (VII) as host material in new types of phosphorescent OLEDs.

The invention also provides compounds of the formulae (VII) and (VIII):

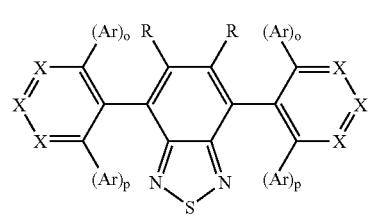

Formula (VII)

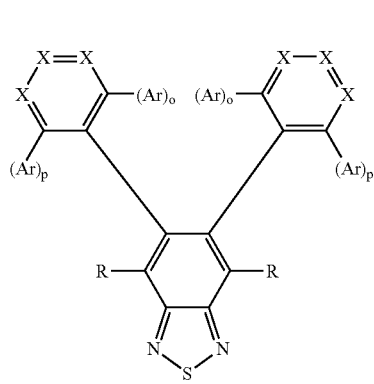

Formula (VIII)

where the symbols and indices R, Ar, $R^1$ and $R^2$ are as defined above and X, o and p have the following meanings:
the radicals X are identical or different on each occurrence and are each C(Ar), CR or N;
o is from 0 to 3, preferably 1;
p is from 1 to 3, preferably 1.

The invention also provides compounds of the formulae (IX), (X) and (XI):

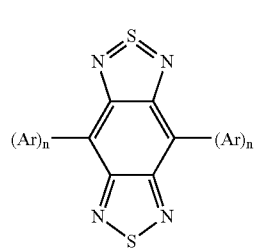

Formula (IX)

Formula (X)

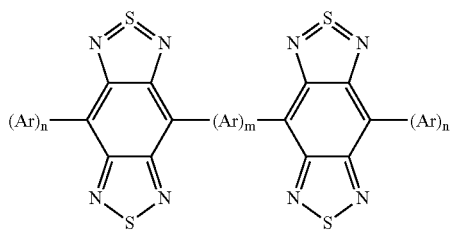

Formula (XI)

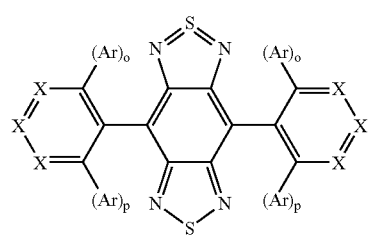

where the symbols and indices X, R, Ar, $R^1$, $R^2$, m, n, o and p are as defined above.

Preferred compounds of the formulae (I) to (XI) are characterized in that the aryl or heteroaryl group Ar has from 3 to 24 carbon atoms, particularly preferably from 3 to 14 carbon atoms.

Preferred compounds of the formula (I) to (XI) are characterized in that the radical Ar is benzene, toluene, xylene, fluorobenzene, difluorobenzene, biphenyl, 1,2- or 1,3- or 1,4-terphenyl, tetraphenyl, naphthyl, fluorene, 9,9'-spirobifluorene, phenanthrene, anthracene, 1,3,5-triphenylbenzene, pyrene, perylene, chrysene, triptycene, [2.2]paracyclophane, pyridine, pyridazine, 4,5-benzopyridazine, pyrimidine, pyrazine, 1,3,5-triazine, pyrrole, indole, 1,2,5- or 1,3,4-oxadiazole, 2,2'- or 4,4'-bipyridyl, quinoline, carbazole, 5,10H-dihydrophenazine, 10H-phenoxazine, phenothiazine, xanthene, 9-acridine, furan, benzofuran, thiophene or benzothiophene.

Even though the information given above describes mainly use of the 2,1,3-benzothiadiazole-containing compounds of the invention in OLEDs, it should be pointed out that these compounds can likewise be used very well in the following devices:

1. Use as electron transport material in electrophotography.
2. Use in photovoltaic devices, e.g. organic photodetectors or organic solar cells, as electron acceptor material or electron transport material.
3. Use in organic integrated circuits (O-ICs).
4. Use in organic field effect transistors (OFETs).
5. Use in organic thin film transistors (OTFTs).
6. Use in further applications, some of which have been mentioned above, e.g. organic solid-state lasers.

These are likewise subject matter of the present invention.

To be able to be used as functional materials, the 2,1,3-benzothiadiazole-containing compounds of the invention are applied in the form of a film to a substrate, generally by means of known methods with which those skilled in the art are familiar, e.g. vacuum vapor deposition, vapor deposition in a carrier gas stream or from solution by spin coating or using various printing processes (e.g. ink jet printing, offset printing, etc).

Some examples of the 2,1,3-benzothiadiazole-containing compounds of the invention are given below:

examples of 2,1,3-benzothiadiazole-containing compounds which have an orange to red emission:

Example R1

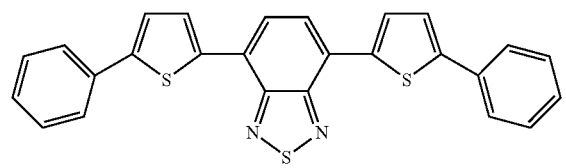

Example R2

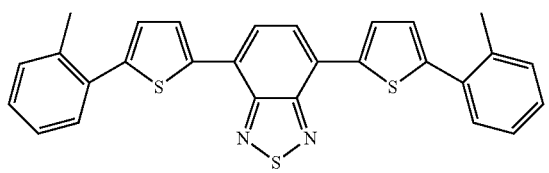

Example R3

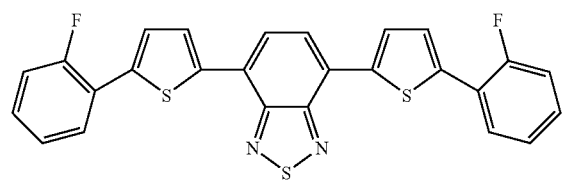

Example R4

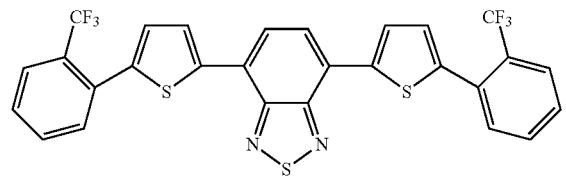

Example R5

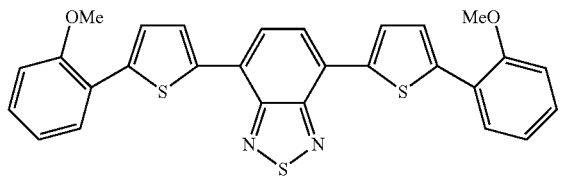

Example R6

-continued
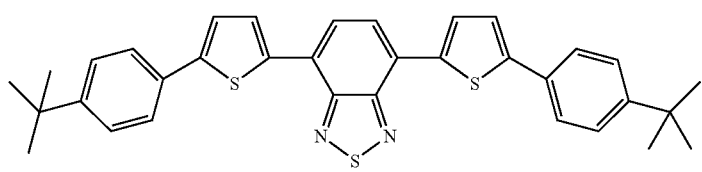
Example R7
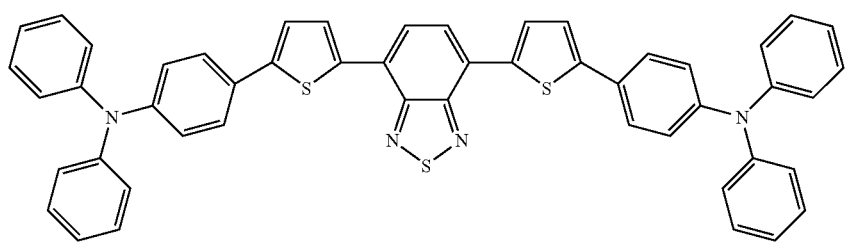
Example R8
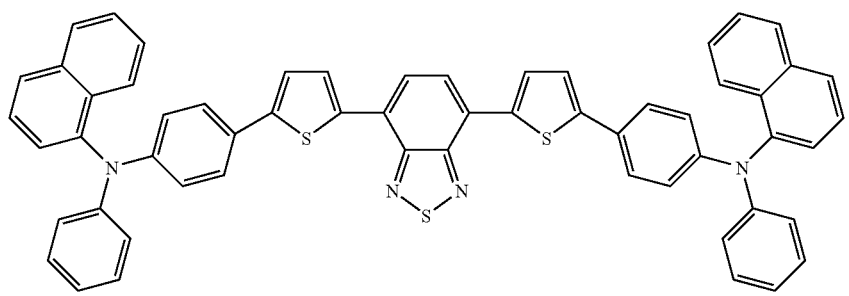
Example R9
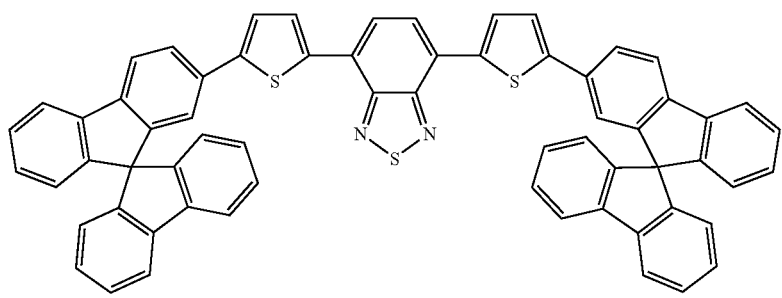
Example R10
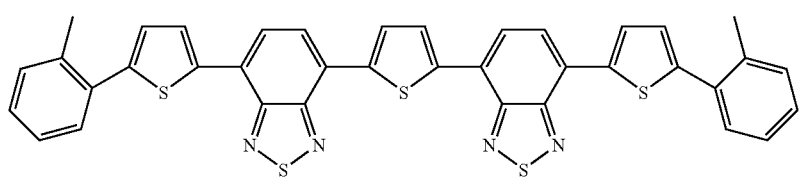
Example R11

Example R12
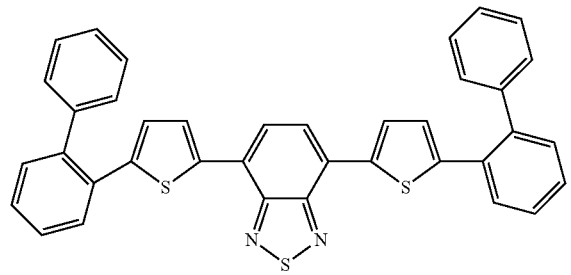
Examples of 2,1,3-benzothiadiazole-containing compounds which have a green to yellow emission:
Example G1
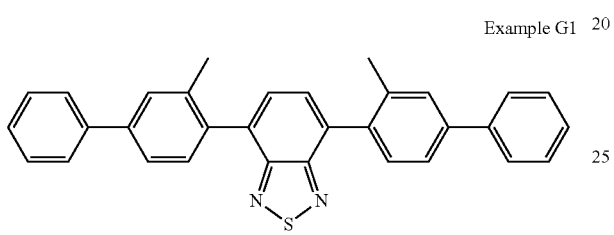
Example G6
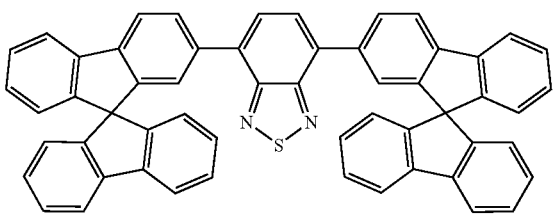
Example G2
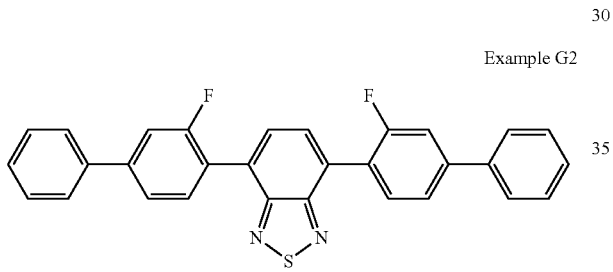
Example G7
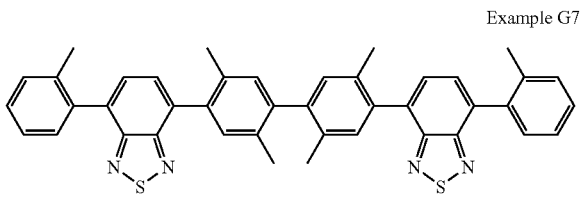
Example G3
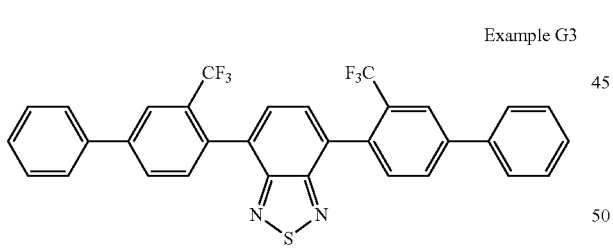
Example G8
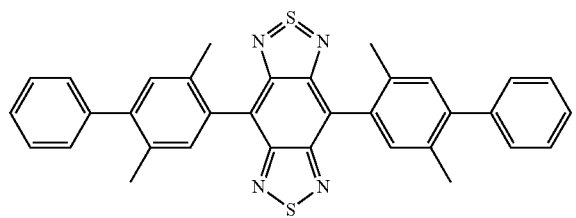
Example G4
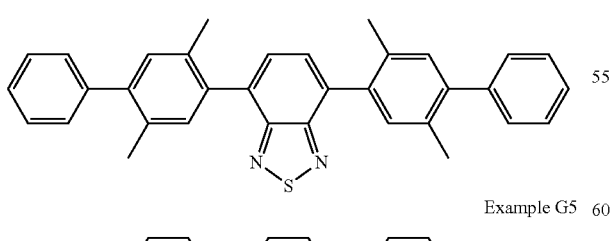
Example G9
Example G10
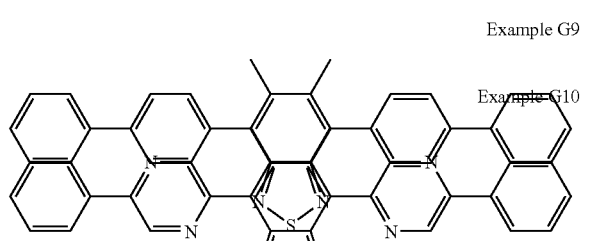
Example G5
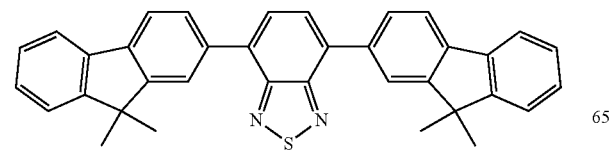
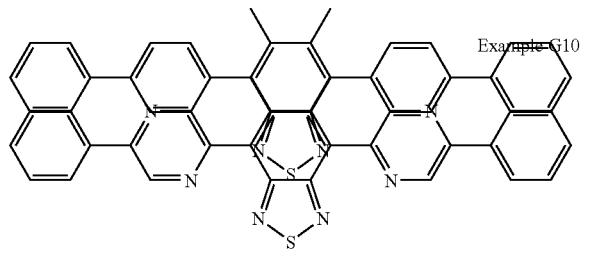
Examples of 2,1,3-benzothiadiazole-containing compounds which have a dark blue to cyan emission:

Example B1
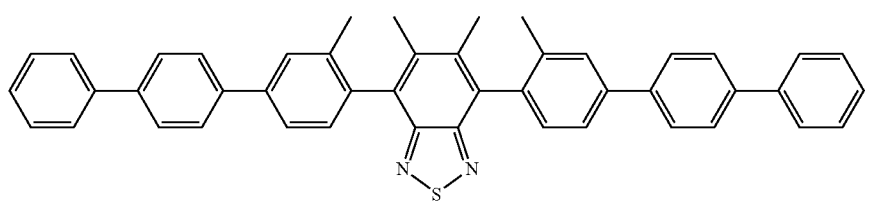
Example B2
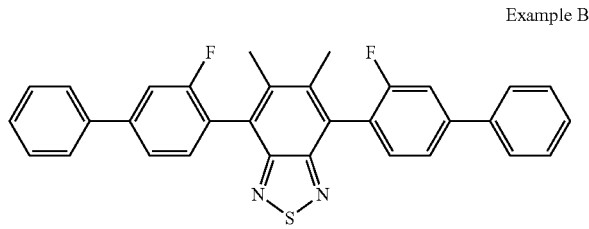
Example B3
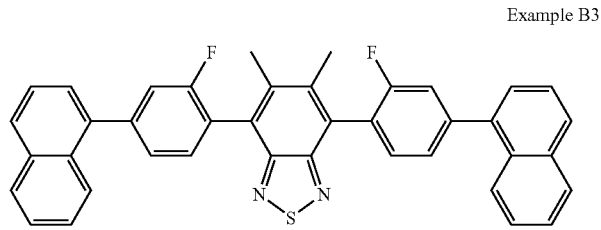
Example B4
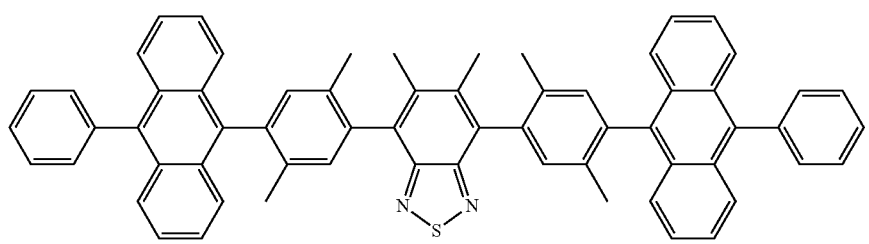
Example B5
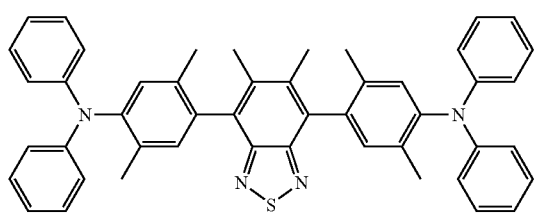
Example B6
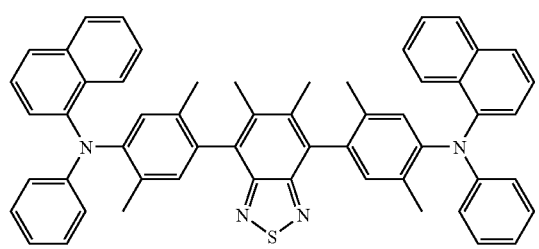
Example B7
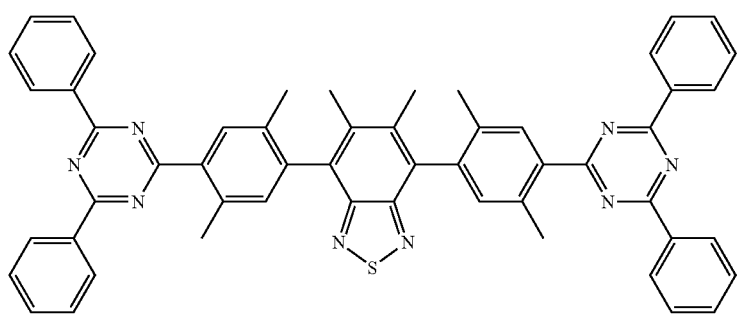
Example B8
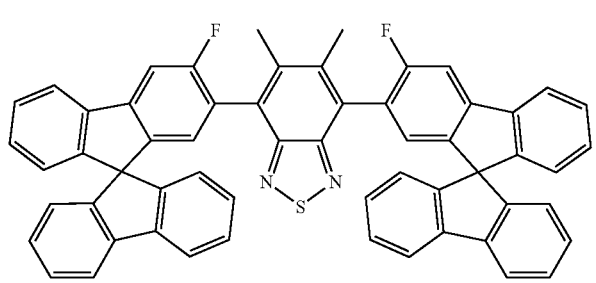

Examples of 2,1,3-benzothiadiazole-containing compounds which are used as ETL, HBL and as host material in the EML are:

Example X1

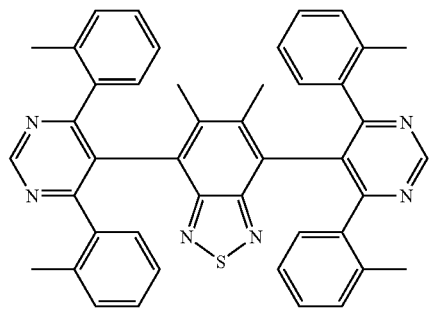

Example X2

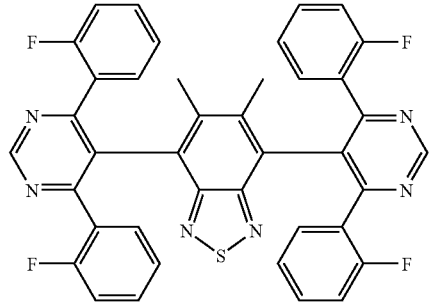

Example X3

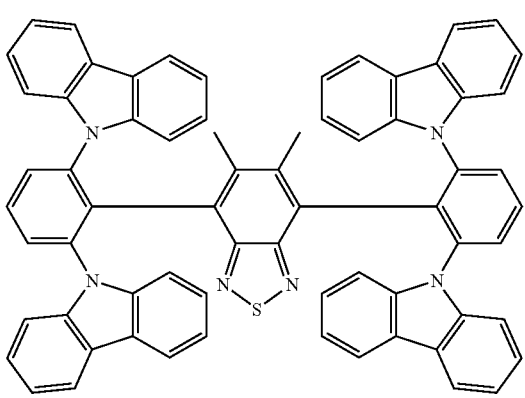

Example X4

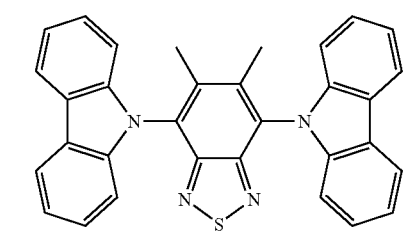

Example X5

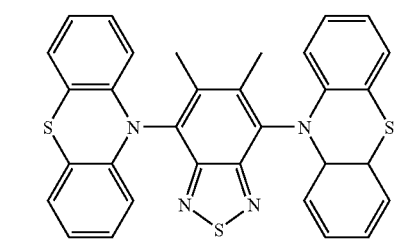

Example X6

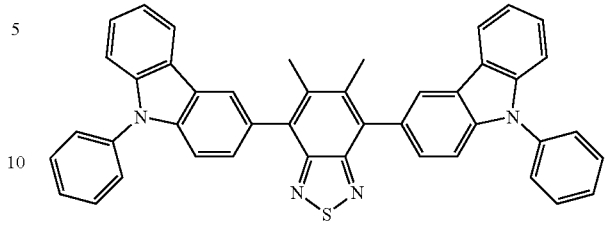

Example X7

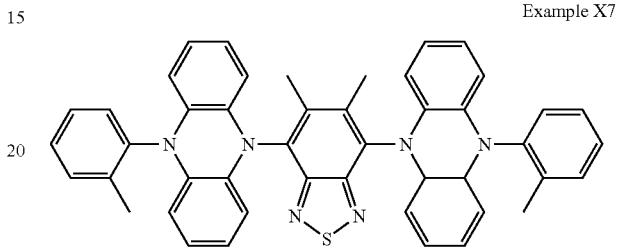

Example 8

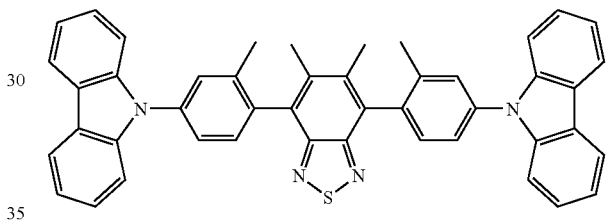

The 2,1,3-benzothiadiazole-containing compounds were prepared by customary methods with which those skilled in the art are familiar, in particular by means of palladium-catalyzed C—C coupling reactions (e.g. Suzuki coupling) or C—N coupling reactions (Hartwig-Buchwald coupling), from brominated 2,1,3-benzothiadiazoles and arylboronic acids or arylamines.

The present invention is illustrated by the following examples, without being restricted thereto. A person skilled in the art will be able to prepare further derivatives according to the invention on the basis of the information given without needing to make an inventive step.

1. Synthesis of 2,1,3-benzothiadiazole-containing Compounds

The following syntheses were carried out under a protected gas atmosphere unless indicated otherwise. The starting materials were procured from ALDRICH [2,1,3-benzothiadiazole, N-bromosuccinimide, thiopheneboronic acid, phenylboronic acid, o-tolylboronic acid, o-fluoroboronic acid, potassium phosphate, sodium cyanide, tri-tert-butylphosphine, palladium(II) acetate, Pd(PPh$_3$)$_4$] or from ALFA[4-chloro-2-methylphenylboronic acid] or prepared by literature methods (4,7-dibromo-2,1,3-benzothiadiazole, 4,7-dibromo-5,6-dimethyl-2,1,3-benzothiadiazole: K. Pilgram, M. Zupan, R. Skiles J. Heterocycl. Chem. 1970, 7, 629).

1.1 Synthesis of Relevant Precursors

EXAMPLE P1

Bis-4,7-(2'-thienyl)-2,1,3-benzothiadiazole 13.52 g (11.7 mmol) of Pd(PPh$_3$)$_4$ were added to a degassed mixture of 52.92 g (180.0 mmol) of 4,7-dibromo-2,1,3-benzothiadiazole, 60.14 g (470.0 mmol) of thiophene-2-boronic acid, 149.02 g (702.0 mmol) of K$_3$PO$_4$, 1000 ml of dioxane and 1000 ml of water. After heating the mixture at 80° C. for 7 hours, 4.58 g (93.6 mmol) of NaCN were added. After cooling to room temperature, the aqueous phase was separated. The organic phase was washed twice with H$_2$O and subsequently dried over Na$_2$SO$_4$. After removal of the solvent and recrystallization of the dark red solid twice from dioxane, the product was obtained in the form of red needles. The yield, at a purity of >99.8% (HPLC), was 43.28 g (144.1 mmol) (80.0%).

$^1$H NMR (CDCl$_3$, 500 MHz): [ppm]=8.11 (dd, $^3J_{HH}$=3.7 Hz, $^4J_{HH}$=1.0 Hz, 2H), 7.89 (s, 2H), 7.46 (dd, $^3J_{HH}$=5.2 Hz, $^4J_{HH}$=1.0 Hz, 2H), 7.21 (dd, $^3J_{HH}$=5.2 Hz, $^3J_{HH}$=3.7 Hz, 2H).

EXAMPLE P2

Bis-4,7-(5'-bromo-2'-thienyl)-2,1,3-benzothiadiazole

A solution of 7.72 g (25.7 mmol) of bis-4,7-(2'-thienyl)-2,1,3-benzothiadiazole in 770 ml of chloroform was admixed with 9.51 g (54.0 mmol) of N-bromosuccinimide at room temperature with exclusion of light. The mixture was stirred for 6 hours and was subsequently evaporated to a volume of 100 ml, admixed with 300 ml of ethanol, the solid was filtered off with suction and washed three times with 100 ml of ethanol. After drying under reduced pressure (70° C., 1 mbar), the residue was recrystallized three times from DMF. The product was obtained in the form of red crystals. The yield, at a purity of >99.8% (HPLC), was 10.31 g (22.5 mmol) (87.5%).

$^1$H NMR (DMSO-d$_6$, 500 MHz): [ppm]=8.17 (s, 2H), 7.95 (d, $^3J_{HH}$=4.2 Hz, 2H), 7.40 (d, $^3J_{HH}$=4.2 Hz, 2H).

EXAMPLE P3

Bis-4,7-(4-chloro-2-methylphenyl)-5,6-dimethyl-2,1,3-benzothiadiazole

A well-stirred, degassed suspension of 91.13 g (283.0 mmol) of 4,7-dibromo-5,6-dimethyl-2,1,3-benzothiadiazole, 125.41 g (736.0 mmol) of 4-chloro-2-methylbenzenebornic acid and 300.19 g (2832.0 mmol) of Na$_2$CO$_3$ in a mixture of 1800 ml of water and 1800 ml of dioxane was admixed with 809 mg (0.70 mmol) of Pd(PPh$_3$)$_4$ and subsequently refluxed for 16 hours. After cooling, the precipitated solid was filtered off with suction, washed three times with 300 ml of water and three times with 300 ml of ethanol. After drying, the solid was recrystallized twice from 150 ml of toluene and 260 ml of ethanol. The product was obtained in the form of colorless crystals. The yield, at a purity of >99.6% (HPLC), was 98.57 g (238.4 mmol) (84.2%).

$^1$H NMR (CDCl$_3$, 500 MHz): [ppm]=7.28, 7.27 (2×s, 2H), 7.19, 7.18 (2×br. s, 2H), 7.06, 7.03 (2×br. s. 2H), 2.23 (s, 6H), 1.99, 1.98 (2×s, 6H).

1.2 Synthesis of Red Emitters:

EXAMPLE R1

Bis-4,7-(5'-phenyl-2'-thienyl)-2,1,3-benzothiadiazole

A degassed mixture of 4.53 g (10.0 mmol) of bis-4,7-(2'-bromo-5'-thienyl)-2,1,3-benzothiadiazole (example P2), 3.66 g (30.0 mmol) of benzeneboronic acid, 8.92 g (42.0 mmol) of K$_3$PO$_4$ and 1.16 g (1.0 mmol) of Pd(PPh$_3$)$_4$ in 400 ml of dioxane and 400 ml of water was heated at 80° C. for 7 hours. After cooling, the mixture was admixed with 0.49 g (10.0 mmol) of NaCN, and after stirring for 15 minutes the aqueous phase was separated off, the organic phase was washed twice with H$_2$O and subsequently dried over Na$_2$SO$_4$. After removal of the solvent and recrystallization from DMF twice, the product was obtained in the form of red needles. The yield, at a purity of >99.9% (HPLC), was 4.31 g (9.5 mmol) (95.2%). $^1$H NMR (DMSO-d$_6$, 500 MHz): [ppm]=8.21 (d, $^3J_{HH}$=4.0 Hz, 2H), 8.18 (s, 2H), 7.82 (m, 2H), 7.69 (d, $^3J_{HH}$=4.0 Hz, 2H), 7.47 (m, 4H), 7.37 (m, 4H). Mp.: 229° C.

EXAMPLE R2

Bis-4,7-(5'-(2-methylphenyl)-2'-thienyl)-2,1,3-benzothiadiazole

This was prepared in a manner analogous to example R1. Instead of the benzeneboronic acid, 4.08 g (30.0 mmol) of 2-methylphenylboronic acid were used. The yield, at a purity of >99.9% (HPLC), was 4.37 g (9.1 mmol) (91.0%).

$^1$H NMR (CDCl$_3$, 500 MHz): [ppm]=8.15 (d, $^3J_{HH}$=4.0 Hz, 2H), 7.91 (s, 2H), 7.52 (m, 2H), 7.29 (m, 6H), 7.19 (d, $^3J_{HH}$=4.0 Hz, 2H), 2.53 (s, 6H). Mp.: 198° C.

EXAMPLE R3

Bis-4,7-(5'-(2-fluorophenyl)-2'-thienyl)-2,1,3-benzothiadiazole

This was prepared in a manner analogous to example R1. Instead of the benzeneboronic acid, 4.20 g (30.0 mmol) of 2-fluorophenylboronic acid were used. The yield, at a purity of >99.9% (HPLC), was 4.28 g (7.2 mmol) (72.0%).

$^1$H NMR (CDCl$_3$, 500 MHz): [ppm]=8.14 (dd, $^3J_{HH}$=4.0 Hz, $^6J_{HF}$=0.67 Hz, 2H), 7.92 (s, 2H), 7.72 (m, 2H), 7.59 (dd, $^3J_{HH}$=4.0 Hz, $^5J_{HF}$=1.34 Hz, 2H), 7.21 (m, 6H). Mp.: 193° C.

EXAMPLE R12

Bis-4,7-(5'-(2-biphenyl)-2'-thienyl)-2,1,3-benzothiadiazole

This was prepared in a manner analogous to example R1. Instead of the benzeneboronic acid, 5.90 g (30.0 mmol) of 2-biphenylboronic acid were used. The yield, at a purity of >99.9% (HPLC), was 5.11 g (8.5 mmol) (84.5%).

$^1$H NMR (CDCl$_3$, 500 MHz): [ppm]=8.88 (dd, 2H), 7.68 (s, 2H), 7.66 (m, 2H), 7.40 (m, 6H), 7.32 (m, 10H), 6.68 (d, 2H). Mp.: 191° C.

1.3 Synthesis of Green Emitters:

EXAMPLE G6

Bis-4,7-(2-spiro-9,9'-bifluorenyl)-2,1,3-benzothiadiazole

This was prepared in a manner analogous to example R1. Instead of the benzeneboronic acid, 10.81 g (30.0 mmol) of spiro-9,9'-bifluorene-2-boronic acid were used.

The yield, at a purity of >99.9% (HPLC), was 5.58 g (7.3 mmol) (73.0%).

$^1$H NMR (CDCl$_3$, 500 MHz): [ppm]=7.93 (s, 2H), 7.84 (m, 4H), 7.80 (m, 2H), 7.67 (m, 2H), 7.48 (m, 2H), 7.38 (m, 4H), 7.35 (m, 2H), 7.11 (m, 6H), 6.85 (m, 2H), 6.71 (m, 6H). Mp. >350° C.

1.4 Synthesis of Blue Emitters:

EXAMPLE B1

Bis-4,7-(2-methylterphenyl)-5,6-dimethyl-2,1,3-benzothiadiazole

A well-stirred, degassed suspension of 41.34 g (100.0 mmol) of bis-4,7-(4-chloro-2-methylphenyl)-5,6-dimethyl-2,1,3-benzothiadiazole, 55.51 g (280 mmol) of biphenyl-4-boronic acid and 136.84 g (420 mmol) of Cs$_2$CO$_3$ in 1500 ml of dioxane was admixed with 243 mg (1.2 mmol) of tri-tert-butylphosphene and 225 mg (1.0 mmol) of palladium (II) acetate and subsequently refluxed for 16 hours. After cooling, 1500 ml of water were added and the precipitate formed was washed three times with 300 ml of water and three times with 300 ml of ethanol. After drying, the solid was recrystallized four times from 300 ml of toluene and 100 ml of ethanol. The product was obtained in the form of colorless crystals. The yield, at a purity of >99.9% (HPLC), was 53.14 g (81.9 mmol) (81.9%).

$^1$H NMR (CDCl$_3$, 500 MHz): [ppm]=7.88 (m, 4H), 7.69 (m, 4H), 7.61 (m, 4H), 7.47 (m, 4H), 7.37 (m, 2H), 7.26, 7.25 (2×s, 2H), 7.14, 7.13 (2×br. s, 2H), 7.09, 7.08 (2×br. s, 2H), 2.22 (s, 6H), 1.97, 1.96 (2×s, 6H). Mp.: 281° C.

2. Production and Characterization of Organic Electroluminescence Devices Comprising the Compounds According to the Invention LEDs were produced by the general method outlined below. This naturally had to be adapted in each individual case to the individual circumstances (e.g. layer thickness variation to achieve optimal efficiency or color).

2.1 General Method of Producing OLEDs

After the ITO-coated substrate (e.g. glass supports, PET film) have been cut to the correct size, they are cleaned in a number of cleaning steps in an ultrasonic bath (e.g. soap solution, Millipore water, isopropanol). To dry the substrates, they are blown with an N$_2$ gun and stored in a desiccator. Before vapor deposition of the organic layers, the substrates are treated by means of an ozone plasma apparatus for about 20 minutes. It can be advisable to use a polymeric hole injection layer as first organic layer. This is generally a conjugated, conductive polymer, e.g. a polyaniline derivative (PANI) or a polythiophene derivative (e.g. PEDOT, BAYTRON P™ from BAYER). This is then applied by spin coating.

The organic layers are applied in order by vapor deposition in a high-vacuum unit. The layer thickness of the respective layer and the deposition rate are monitored and set by means of a crystal oscillator. It is also possible, as described above, for individual layers to consist of more than one compound, i.e. in general, a host material can be doped with a guest material. This is achieved by covaporization from two or more sources.

Electrodes are then applied to the organic layers. This is generally achieved by thermal vapor deposition (Balzer BA360 or Pfeiffer PL S 500).

The transparent ITO electrode is subsequently connected as anode and the metal electrode (e.g. Ca, Yb, Ba—Al) is connected as cathode and the device parameters are determined.

2.2 Process for Producing Red OLEDs

EXAMPLE 1

Red OLED with Emitter Material from Example R1

Using a procedure analogous to the abovementioned general method, a red-emitting OLED having the following structure was produced:

| | |
|---|---|
| PEDOT | 20 nm (applied by spin coating from water; PEDOT procured from BAYER AG; poly[3,4-ethylenedioxy-2,5-thiophene] |
| MTDATA | 20 nm (vapor-deposited; MTDATA procured from SynTec; tris-4,4',4''-(3-methylphenylphenylamino)triphenylamine) |
| S-TAD | 20 nm (vapor-deposited; S-TAD prepared as described in WO99/12888; 2,2',7,7'-tetrakis(diphenylamino)-9,9'-spirobifluorene) |
| AlQ$_3$ | 30 nm (vapor-deposited; AlQ$_3$ procured from SynTec; tris(quinoxalinato)aluminum(III)) and doped with |
| R1 | 10% by weight (vapor-deposited; bis-4,7-(5'-phenyl-2'-thienyl)-2,1,3-benzothiadiazole prepared as described in example R1) |
| AlQ$_3$ | 10 nm (vapor-deposited; AlQ$_3$ procured from SynTec; tris(quinoxalinato)aluminum(III)) |
| Ba | 10 nm as cathode |
| Ag | 100 nm as cathode protection layer |

This unoptimized OLED was characterized in a standard fashion; the measured data are shown in FIGS. 1–3. Apart from the flatness of the efficiency curve, which means that high efficiencies can still be achieved even at very high brightnesses (e.g. 10 000 Cd/m$^2$), the excellent operating life of this OLED is a great advantage.

EXAMPLE 2

Red OLED with Emitter Material from Example R12

Using a procedure analogous to the abovementioned general method, a red-emitting OLED having the following structure was produced:

| | |
|---|---|
| PEDOT | 20 nm (applied by spin coating from water; PEDOT procured from BAYER AG; poly[3,4-ethylenedioxy-2,5-thiophene] |
| MTDATA | 20 nm (vapor-deposited; MTDATA procured from SynTec; tris-4,4',4''-(3-methylphenylphenylamino)triphenylamine) |
| S-TAD | 20 nm (vapor-deposited; S-TAD prepared as described in WO99/12888; 2,2',7,7'-tetrakis(diphenylamino)-9,9'-spirobifluorene) |
| AlQ$_3$ | 30 nm (vapor-deposited; AlQ$_3$ procured from SynTec; tris(quinoxalinato)aluminum(III)) and doped with |
| R12 | 10% by weight (vapor-deposited; bis-4,7-(5'-(2-biphenyl)-2'-thienyl)-2,1,3-benzothiadiazole prepared as described in example R12) |
| AlQ$_3$ | 10 nm (vapor-deposited; AlQ$_3$ procured from SynTec; tris(quinoxalinato)aluminum(III)) |
| Ba | 10 nm as cathode |
| Ag | 100 nm as cathode protection layer |

This unoptimized OLED was characterized in a standard fashion; the measured data are shown in FIGS. 4–6. Apart from the flatness of the efficiency curve, which means that high efficiencies can still be achieved even at very high brightnesses (e.g. 10 000 Cd/m$^2$), the excellent operating life of this OLED is a great advantage.

2.3 Method of Producing Blue OLEDs

EXAMPLE 3

Blue OLED with Emitter Material from Example B1

Using a procedure analogous to the abovementioned general method, a blue-emitting OLED having the following structure was produced:

| | |
|---|---|
| PEDOT | 20 nm (applied by spin coating from water; PEDOT procured from BAYER AG; poly[3,4-ethylenedioxy-2,5-thiophene] |
| MTDATA | 20 nm (vapor-deposited; MTDATA procured from SynTec; tris-4,4',4''-(3-methylphenylphenylamino)triphenylamine) |
| S-TAD | 20 nm (vapor-deposited; S-TAD prepared as described in WO99/12888; 2,2',7,7'-tetrakis(diphenylamino)-9,9'-spirobifluorene) |
| S-DPVBi | 30 nm (vapor-deposited; S-DPVBi prepared as described by H. Spreitzer, H. Schenk, J. Salbeck, F. Weissoertel, H. Riel. W. Ries, Proceedings of SPIE, 1999, Vol. 3797; 2,2',7,7'-tetrakis(2,2'-diphenylvinyl)spiro-9,9'-bifluorene) and doped with |
| B1 | 10% by weight (vapor-deposited; 5,6-dimethylbis-4,7-(2,5-dimethylphenyl)-2,1,3-benzothiadiazole prepared as described in example B1), doped into the above S-DPVBi layer |
| AlQ$_3$ | 10 nm (vapor-deposited; AlQ$_3$ procured from SynTec; tris(quinoxalinato)aluminum(III)) |
| Ba | 10 nm as cathode |
| Ag | 100 nm as cathode protection layer |

This unoptimized OLED was characterized in a standard fashion; the measured data are shown in FIGS. 7 and 8. Apart from the color, a tremendous advantage of this OLED is the flatness of the efficiency curve, which means that high efficiencies can still be achieved even at very high brightnesses (e.g. 10 000 Cd/m$^2$). This is of critical importance especially for use in passive matrix displays.

The invention claimed is:

1. A compound which belong to the idealized point group $S_n$, $C_n$, $C_{nv}$, $C_{nh}$, $D_n$, $D_{nh}$ or $D_{nd}$ with n=2, 3, 4, 5 or 6, the molar masses are in the range from 450 g/mol to 5000 g/mol and the melting points are above a temperature of 190° C., having the Formula (II) or (III), Formula (II)

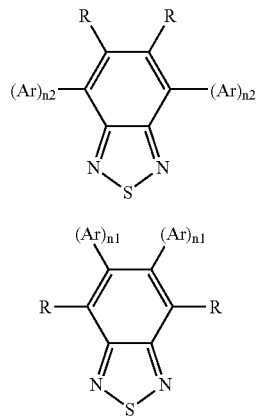

Formula (III)

where the symbols and indices have the following meanings:

the radicals R are identical on each occurrence and are each H, F, CN, a straight-chain or branched or cyclic alkyl or alkoxy group having from 1 to 20 carbon atoms, where one or more nonadjacent $CH_2$ groups may be replaced by —O—, —S—, —$NR^1$ or —$CONR^2$— and one or more H atoms may be replaced by F;

the radicals Ar are identical or different on each occurrence and are each an aryl or heteroaryl group which has from 3 to 30 carbon atoms and may be substituted by one or more nonaromatic radicals R; where a plurality of substituents R, both on the same ring and on the two different rings, may in turn together form a further monocyclic or polycyclic ring system;

$R^1$, and $R^2$ are identical or different and are each H or an aliphatic or aromatic hydrocarbon radical having from 1 to 20 carbon atoms;

n2 is from 3 to 10, n1 is from 1 to 10, and with the proviso that they do not contain a macrocycle.

2. A compound which belong to the idealized point group $S_n$, $C_n$, $C_{nv}$, $D_n$, $D_{nh}$ or $D_{nd}$ with n=2, 3, 4, 5 or 6, the molar masses are in the range from 450 g/mol to 5000 g/mol and the melting points are above a temperature of 190° C., described by the formula (IV)

Formula (IV)

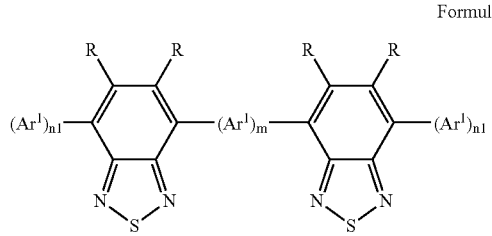

where the symbols and indices have the following meanings:

the radicals R are identical on each occurrence and are each H, F, CN, a straight-chain or branched or cyclic alkyl or alkoxy group having from 1 to 20 carbon atoms, where one or more nonadjacent $CH_2$ groups may be replaced by —O—, —S—, —$NR^1$ or —$CONR^2$— and one or more H atoms may be replaced by F;

the radicals $Ar^1$ are identical or different on each occurrence and are each an aryl or heteroaryl group which are benzene, toluene, xylene, fluorobenzene, difluorobenzene, biphenyl, 1,2- or 1,3- or 1,4-terphenyl, tetraphenyl, naphthyl, fluorene, 9,9'-spirobifluorene, phenanthrene, anthracene, 1,3,5-triphenylbenzene, pyrene, perylene, chrysene, triptycene, [2.2]paracyclophane, pyridine, pyridazine, 4,5-benzopyridazine, pyrimidine, pyrazine, 1,3,5-triazine, pyrrole, indole, 1,2,5- or 1,3,4-oxadiazole, 2,2'- or 4,4'-bipyridyl, quinoline, carbazole, 5,10H-dihydrophenazine, 10H-phenoxazine, phenothiazine, xanthene, 9-acridine, furan, benzofuran, or benzothiophene which may be substituted by one or more nonaromatic radicals R; where a plurality of substituents R, both on the same ring and on the two different rings, may in turn together form a further monocyclic or polycyclic ring system;

$R^1$, and $R^2$ are identical or different and are each H or an aliphatic or aromatic hydrocarbon radical having from 1 to 20 carbon atoms;

m is from 0 to 4;

n1 is from 1 to 10.

3. A compound which belong to the idealized point group $S_n$, $C_n$, $C_{nv}$, $D_n$, $D_{nh}$ or $D_{nd}$ with n=2, 3, 4, 5 or 6, the molar masses are in the range from 450 g/mol to 5000 g/mol and the melting points are above a temperature of 190° C., described by the formula (V), (VI), (VII), (VIII), (IX) (X) or (XI)

Example (V)

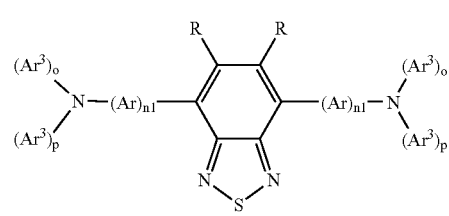

Example (VI)

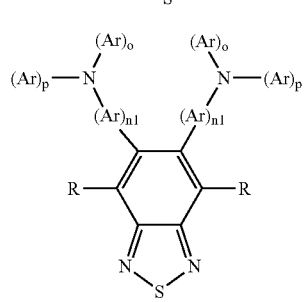

Formula (VII)

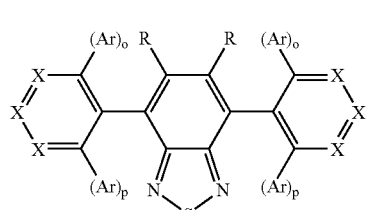

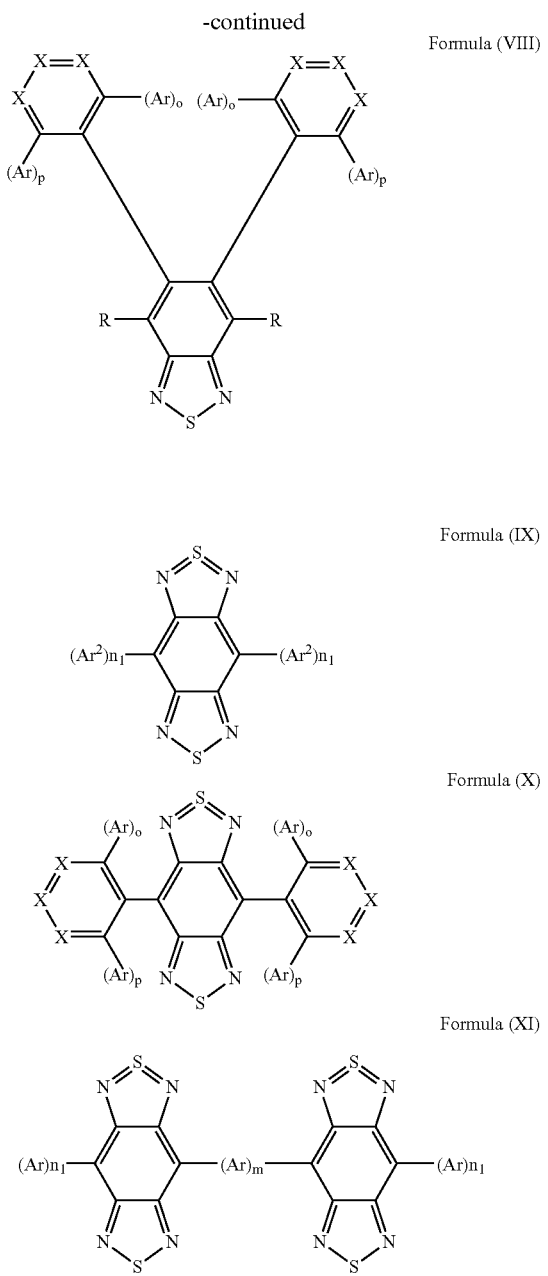

where the symbols and indices have the following meanings:

the radicals R are identical on each occurrence and are each H, F, CN, a straight-chain or branched or cyclic alkyl or alkoxy group having from 1 to 20 carbon atoms, where one or more nonadjacent $CH_2$ groups may be replaced by —O—, —S—, —$NR^1$ or —$CONR^2$— and one or more H atoms may be replaced by F;

the radicals Ar are identical or different on each occurrence and are each an aryl or heteroaryl group which has from 3 to 30 carbon atoms and may be substituted by one or more nonaromatic radicals R; where a plurality of substituents R, both on the same ring and on the two different rings, may in turn together form a further monocyclic or polycyclic ring system;

the radicals $Ar^3$ are identical or different on each occurrence and are each an aryl or heteroaryl group which are toluene, xylene, fluorobenzene, difluorobenzene, biphenyl, 1,2- or 1,3- or 1,4-terphenyl, tetraphenyl, naphthyl, fluorene, 9,9'-spirobifluorene, phenanthrene, anthracene, 1,3,5-triphenylbenzene, pyrene, perylene, chrysene, triptycene, [2.2]paracyclophane, pyridine, pyridazine, 4,5-benzopyridazine, pyrimidine, pyrazine, 1,3,5-triazine, pyrrole, indole, 1,2,5- or 1,3,4-oxadiazole, 2,2'- or 4,4'-bipyridyl, quinoline, carbazole, 5,10H-dihydrophenazine, 10H-phenoxazine, phenothiazine, xanthene, 9-acridine, furan, benzofuran, thiophene or benzothiophene which may be substituted by one or more nonaromatic radicals R; where a plurality of substituents R, both on the same ring and on the two different rings, may in turn together form a further monocyclic or polycyclic ring system;

the radicals $Ar^2$ are identical or different on each occurrence and are each an aryl or heteroaryl group which has from 3 to 30 carbon atoms and may be substituted by one or more nonaromatic radicals $R^3$; where a plurality of substituents $R^3$, both on the same ring and on the two different rings, may in turn together form a further monocyclic or polycyclic ring system;

$R^1$, and $R^2$ are identical or different and are each H or an aliphatic or aromatic hydrocarbon radical having from 1 to 20 carbon atoms;

the radicals X are identical or different on each occurrence and are each C(Ar), CR or N;

the radicals $R^3$ are identical on each occurrence and are each H, F, CN, a straight-chain or branched or cyclic alkyl having from 1 to 20 carbon atoms, where one or more nonadjacent $CH_2$ groups may be replaced by —O—, —S—, —$NR^1$ or —$CONR^2$— and one or more H atoms may be replaced by F;

n1 is from 1 to 10;

o is from 1 to 3; and p is from 1 to 3.

4. The compound as claimed in claim 3, which is described by the formula (VII) or (VIII).

5. The compound as claimed in claim 3, where the compound is described by the formula (IX), (X), or (XI),
and the molar masses are in the range from 450 g/mol to 5000 g/mol and the melting points are above a temperature of 190° C., with the proviso that they do not contain a macrocycle.

6. The compound as claimed in claim 1, characterized in that the radical Ar is benzene, toluene, xylene, fluorobenzene, difluorobenzene, biphenyl, 1,2- or 1,3- or 1,4-terphenyl, tetraphenyl, naphthyl, fluorene, 9,9'-spirobifluorene, phenanthrene, anthracene, 1,3,5-triphenylbenzene, pyrene, perylene, chrysene, triptycene, [2.2]paracyclophane, pyridine, pyridazine, 4,5-benzopyridazine, pyrimidine, pyrazine, 1,3,5-triazine, pyrrole, indole, 1,2,5- or 1,3,4-oxadiazole, 2,2'- or 4,4'-bipyridyl, quinoline, carbazole, 5,10H-dihydrophenazine, 10H-phenoxazine, phenothiazine, xanthene, 9-acridine, furan, benzofuran, thiophene or benzothiophene.

7. An electronic component comprising at least one compound as claimed in claim 1.

8. An electronic component comprising at least one compound as claimed in claim 2.

9. An electronic component comprising at least one compound as claimed in claim 3.

10. The compound as claimed in claim 1, wherein n1 is from 1 to 6.

11. The compound as claimed in claim 1, wherein n1 is from 1,2 or 3.

12. The compound as claimed in claim 2, wherein m is from 1 or 2 and n1 is from 1, 2, or3.

13. The compound as claimed in claim 3, wherein the compound is of the formula (V) or (VI) and n1 is from 1, 2 or 3; o is 1; and p is 1.

14. The compound as claimed in claim 5, wherein m is from 1 or 2; n1 is from 1, 2 or 3.

15. The compound as claimed in claim 14, characterized in that the radical Ar is benzene, toluene, xylene, fluorobenzene, difluorobenzene, biphenyl, 1,2- or 1,3- or 1,4-terphenyl, tetraphenyl, naphthyl, fluorene, 9,9'-spirobifluorene, phenanthrene, anthracene, 1,3,5-triphenylbenzene, pyrene, perylene, chrysene, triptycene, [2.2]paracyclophane, pyridine, pyridazine, 4,5-benzopyridazine, pyrimidine, pyrazine, 1,3,5-triazine, pyrrole, indole, 1,2,5- or 1,3,4-oxadiazole, 2,2'- or 4,4'-bipyridyl, quinoline, carbazole, 5,10H-dihydrophenazine, 10H-phenoxazine, phenothiazine, xanthene, 9-acridine, furan, benzofuran, thiophene or benzothiophene.

16. An organic electroluminescence and/or electrophosphorescence devices which comprises the compound as claimed in claim 1.

17. An emission layer (EML), a host material in electroluminescence and/or electrophosphorescence devices, as electron transport layers (ETLs) and/or hole-blocking layers (HBLs) which comprises the compound as claimed in claim 1.

18. An electron transport material in electrophotography, electron acceptor material or electron transport material in photovoltaic devices which comprises the compound as claimed in claim 1.

19. An organic photodetector, organic solar cells, a transport material in organic ICs (organic integrated circuits), a transport material and/or dopant in organic field effect transistors (OTFTs), a transport material and/or dopant in organic thin-film transistors or an organic solid-state lasers which comprises the compound as claimed in claim 1.

20. An electronic component comprising at least one compound as claimed in claim 2.

21. An electronic component comprising at least one compound as claimed in claim 3.

* * * * *

UNITED STATES PATENT AND TRADEMARK OFFICE
CERTIFICATE OF CORRECTION

| | |
|---|---|
| PATENT NO. | : 7,223,484 B2 |
| APPLICATION NO. | : 10/519967 |
| DATED | : May 29, 2007 |
| INVENTOR(S) | : Philipp Stössel et al. |

It is certified that error appears in the above-identified patent and that said Letters Patent is hereby corrected as shown below:

In the Claims:

In Claim 3, in column 26, on line 29, "$S_n$, $C_n$, $C_{nv}$, $D_n$, $D_{nh}$ or $D_{nd}$ with n=2,3,4,5 or 6, the molar" should read -- $S_n$, $C_n$, $C_{nv}$, $C_{nh}$, $D_n$, $D_{nh}$ or $D_{nd}$ with n=2,3,4,5 or 6, the molar--.

In Claim 3, in column 26, on line 36, "Example (V)" should read -- Formula (V)--.

In Claim 3, in column 26, Formula (V) and Formula (VI)

"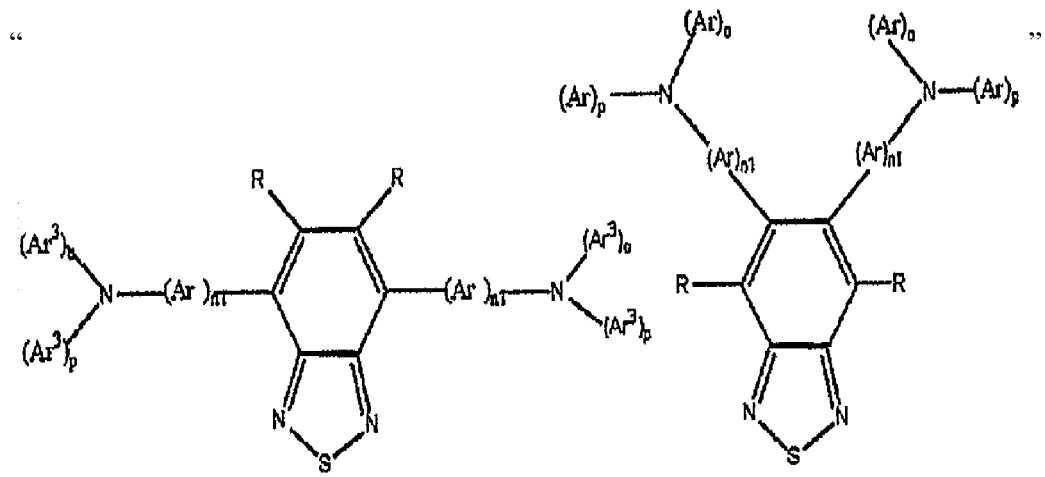"

UNITED STATES PATENT AND TRADEMARK OFFICE
CERTIFICATE OF CORRECTION

| | | |
|---|---|---|
| PATENT NO. | : 7,223,484 B2 | Page 2 of 2 |
| APPLICATION NO. | : 10/519967 | |
| DATED | : May 29, 2007 | |
| INVENTOR(S) | : Philipp Stössel et al. | |

It is certified that error appears in the above-identified patent and that said Letters Patent is hereby corrected as shown below:

In Claim 3, in column 26, ...(cont'd)

should read

--

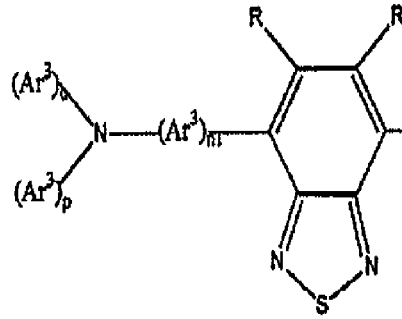

Formula (V)

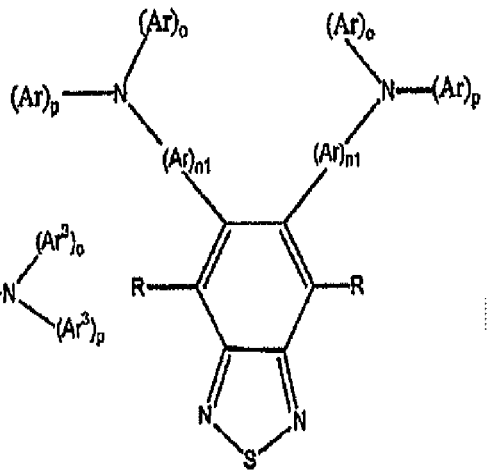

Formula (VI) --.

In Claim 12, in column 29, on line 4, "from 1 or 2 and n1 is from 1, 2, or3."

should read -- from 1 or 2 and n1 is from 1, 2, or 3.--.

Signed and Sealed this

Eighteenth Day of September, 2007

JON W. DUDAS
*Director of the United States Patent and Trademark Office*